US010226508B2

(12) United States Patent
Grönberg et al.

(10) Patent No.: US 10,226,508 B2
(45) Date of Patent: Mar. 12, 2019

(54) TREATMENT OF CHRONIC ULCERS

(71) Applicant: Promore Pharma AB, Solna (SE)

(72) Inventors: Alvar Grönberg, Solna (SE); Christine Dieterich, Solna (SE); Margit Mahlapuu, Solna (SE)

(73) Assignee: Promore Pharma AB, Solna (SE)

( * ) Notice: Subject to any disclaimer, the term of this patent is extended or adjusted under 35 U.S.C. 154(b) by 0 days.

(21) Appl. No.: 15/037,199

(22) PCT Filed: Nov. 19, 2014

(86) PCT No.: PCT/GB2014/053415
§ 371 (c)(1),
(2) Date: May 17, 2016

(87) PCT Pub. No.: WO2015/075441
PCT Pub. Date: May 28, 2015

(65) Prior Publication Data
US 2016/0271217 A1    Sep. 22, 2016

(30) Foreign Application Priority Data
Nov. 19, 2013 (WO) ............... PCT/GB2013/053053

(51) Int. Cl.
*A61K 38/17* (2006.01)
*A61L 15/44* (2006.01)
*A61K 9/00* (2006.01)
*A61K 9/06* (2006.01)
*A61K 47/32* (2006.01)
*A61L 26/00* (2006.01)

(52) U.S. Cl.
CPC ........ *A61K 38/1729* (2013.01); *A61K 9/0014* (2013.01); *A61K 9/06* (2013.01); *A61K 38/17* (2013.01); *A61K 47/32* (2013.01); *A61L 15/44* (2013.01); *A61L 26/0019* (2013.01); *A61L 26/0085* (2013.01); *A61L 2300/252* (2013.01); *A61L 2300/404* (2013.01); *A61L 2300/412* (2013.01)

(58) Field of Classification Search
CPC ............ A61K 38/1709; A61K 38/1729; C07K 14/47; C07K 14/4723
See application file for complete search history.

(56) References Cited

U.S. PATENT DOCUMENTS

| 5,271,943 | A | * | 12/1993 | Bogart | A61L 26/0014 424/443 |
| 6,201,164 | B1 | * | 3/2001 | Wulff | A61K 9/0014 602/41 |
| 7,262,179 | B2 | * | 8/2007 | Court | A61K 31/728 514/54 |
| 7,452,864 | B2 | | 11/2008 | Stahle-Backdahl et al. | |
| 8,012,933 | B2 | | 9/2011 | Stahle-Backdahl et al. | |
| 8,506,994 | B2 | | 8/2013 | Stahle-Backdahl et al. | |
| 8,507,496 | B2 | * | 8/2013 | Bar-Or | A61K 31/496 514/252.12 |
| 8,936,807 | B2 | | 1/2015 | Stahle-Backdahl et al. | |
| 9,125,875 | B2 | | 9/2015 | Stahle-Backdahl et al. | |
| 2002/0169279 | A1 | | 11/2002 | Montelaro et al. | |
| 2008/0226724 | A1 | * | 9/2008 | Ji | A61K 9/0014 424/486 |
| 2011/0111035 | A1 | * | 5/2011 | Washburn | A61K 47/48215 424/488 |
| 2013/0236571 | A1 | * | 9/2013 | Magdassi | A61Q 19/08 424/678 |
| 2015/0174196 | A1 | * | 6/2015 | Gourdie | C07K 7/08 424/422 |

FOREIGN PATENT DOCUMENTS

| EP | 0935965 A1 | 8/1999 |
| WO | 9640221 A1 | 12/1996 |
| WO | 2002060501 A2 | 8/2002 |
| WO | WO-2004067025 A1 | 8/2004 |
| WO | 2007085884 A1 | 8/2007 |
| WO | WO-2009001087 A2 | 12/2008 |
| WO | 2009083203 A2 | 7/2009 |
| WO | 2011056116 A1 | 5/2011 |

OTHER PUBLICATIONS

Boulton et al, The global burden of diabetic foot disease, *Lancet*, 366:1719-1724, 2005.
Carretero et al, In vitro and In vivo Wound Healing-Promoting Activities of Human Cathelicidin LL-37, *J. Invest. Dermatol.*, 128:223-236, 2008.
Dressel et al, Differential expression of antimicrobial peptides in margins of chronic wounds, *Exp. Dermatol.*, 19:628-632, 2010.
Grönberg et al; Stability of the Cathelicidin Peptide LL-37 in a Non-healing Wound Environment, *Acta Dermato-Venereologica* 91(5):511-515, Sep. 2011.
Grönberg, et al., Treatment with LL-37 is safe and effective in enhancing healing of hard-to-heal venous leg ulcers: a randomized, placebo-controlled clinical trial, *Wound Rep. Reg.* 22:613-621, 2014.
Heilborn et al, The Cathelicidin Anti-Microbial Peptide LL-37 is Involved in Re-Epithelialization of Human Skin Wounds and is Lacking in Chronic Ulcer Epithelium, *J. Invest. Dermatol.*, 120(3):379-389, 2003.

(Continued)

*Primary Examiner* — Jeffrey E. Russel
(74) *Attorney, Agent, or Firm* — McCarter & English, LLP; Steven G. Davis; Mei Bai

(57) ABSTRACT

The present invention provides a pharmaceutical formulation comprising LL-37 or a pharmaceutically-acceptable salt thereof and one or more pharmaceutically-acceptable diluent or carrier system, for use in a method of treatment of a chronic ulcer wound (such as a hard-to-heal venous leg ulcer or a diabetic foot ulcer), which method comprises:
(a) topical application of the formulation to the ulcer; followed by
(b) application of a dressing, and
wherein the application of the formulation provides for a dose of LL-37 at the wound site that is below about 80 µg of LL-37 applied per $cm^2$ of wound area, and/or below about 26.7 µg of LL-37 applied per $cm^2$ of wound area, per day of treatment.

14 Claims, 1 Drawing Sheet
Specification includes a Sequence Listing.

(56) References Cited

OTHER PUBLICATIONS

Koczulla et al, An angiogenic role for the human peptide antibiotic LL-37/hCAP-18, *J. Clin. Invest.*, 111(11):1665-1672, 2003.
Murakami et al, Cathelicidin Antimicrobial Peptides are Exprssed in Salivary Glands and Saliva, *J. Dent. Res.*, 81(12):845-850, 2002.
Pergamum AB, Press Release: Pergamum announces final data from Phase I/II study of LL-37 in patients with chronic leg ulcers, Oct. 10, 2013, available at: http://pergamum.com/blog/pergamum-announces-final-data-phase-iii-study-II-37-patients-chronic-leg-ulcers/.
Posnett, et al, The resource impact of wounds on health-care providers in Europe, *Journal of Wound Care*, 18(4):154-159, 2009.
Prompers et al, Resource utiisation and costs associated with the treatment of diabetic foot ulcers. Prospective data from the Eurodiale Study, *Diabetologia*, 51:1826-1834, 2008.
Ragnarson Tennvall et al, Prevention of diabetes-related foot ulcers and amputations: a cost-utility analysis based on Markov model simulations, *Diabetologia*, 44:2077-2087, 2001.
Ramos et al, Wound healing activity of the human antimicrobial peptide LL37, *Peptides,* 32(7):1469-1476, 2011.
Ramsey et al, Incidence, Outcomes, and Cost of Foot Ulcers in Patients with Diabetes, *Diabetes Care,* 22(3):382-387, 1999.
Rivas-Santiago et al, Expression of antimicrobial peptides in diabetic foot ulcer, *J. Derm. Sci.,* 65(1):19-26, 2012.
Schaller-Bals et al, Increased Levels of Antimicrobial Peptides in Tracheal Aspirates of Newborn Infants during Infection, *Am. J. Respir. Crit. Care Med.,* 165:992-995; 2002.
Singh et al, Preventing Foot Ulcers in Patients with Diabetes, *JAMA,* 293(2):217-228, 2005.
Snyder, Treatment of nonhealing ulcers with allografts, *Clin. Dermatol.,* 23:388-395, 2005.
Steinstraesser et al, Innate Defense Regulator Peptide 1018 in Wound Healing and Wound Infection, *PLoS ONE,* 7(8):e39373, 2012.
Sørensen et al, Processing of seminal plasma hCAP-18 to ALL-38 by gastricsin. A Novel Mechanism of Generating Antimicrobial Peptides in Vagina, *J. Biol. Chem.,* 278(31):28540-28546, 2003.
Valencia et al, Chronic venous insufficiency and venous leg ulceration, *J. Am. Acad. Dermatol.,* 44(3):401-424, 2001.

* cited by examiner

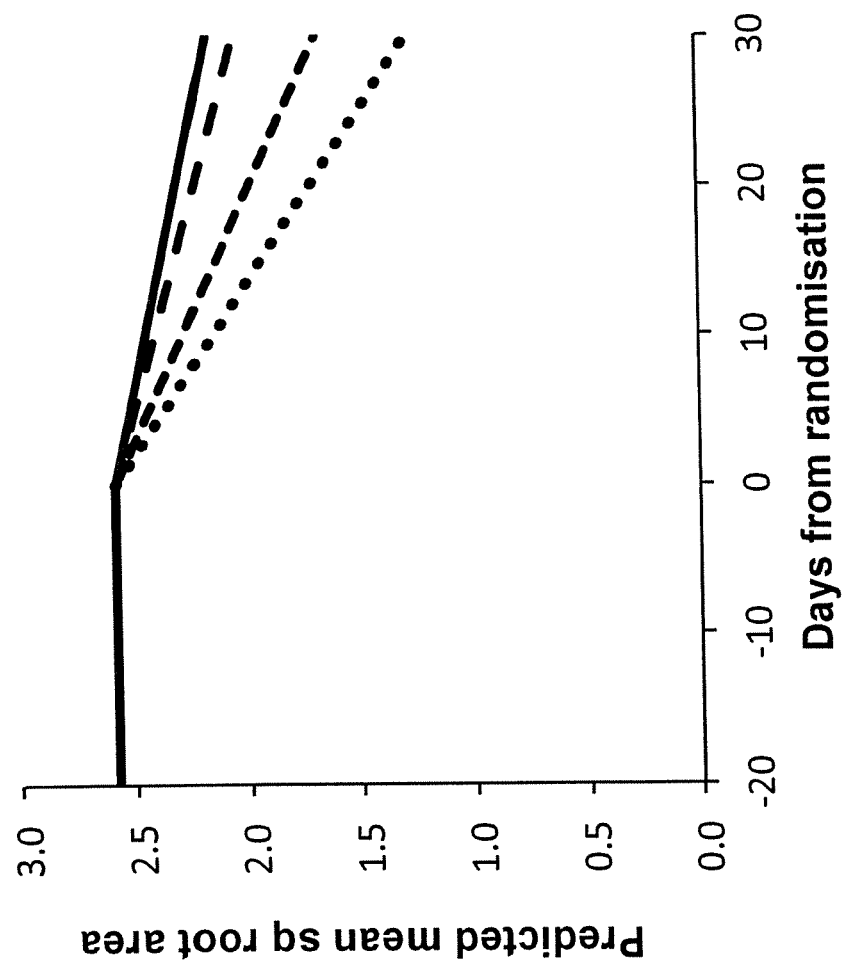

TREATMENT OF CHRONIC ULCERS

RELATED APPLICATIONS

This application is a U.S. National Stage Application of International Application No. PCT/GB2014/053415 filed Nov. 19, 2014, which in turn claims the benefit of International Application No. PCT/GB2013/053053 filed Nov. 19, 2013.

FIELD OF INVENTION

The present invention relates to methods of using wound care products. In particular, the invention provides for the treatment of chronic ulcers.

BACKGROUND

Wound healing is a dynamic pathway that optimally leads to restoration of tissue integrity and function. A "chronic" wound is one in which the healing process is prolonged and incomplete, resulting in a lack of restoration of integrity. Chronic wounds are a challenge to the patient, healthcare professionals, and the healthcare system, and significantly impair the quality of life for millions of people. Long-term, repetitive treatment is required, which imparts an enormous burden on society in terms of lost productivity and healthcare budgets.

Hard-to-heal (HTH) or chronic ulcers are a class of chronic wound. HTH ulcers of the leg and the foot, are often painful, stigmatising and have a negative impact on functional ability.

Venous leg ulcers (VLUs) are chronic skin and subcutaneous ulcerations that occur on the lower leg, between the knee and the malleolus. The Swedish Medical Product Agency defines a VLU as one that is below the knee caused by venous insufficiency, which does not heal within six weeks of standard therapy (i.e. traditional wound care products, such as low technology gauze-based dressings, woven and non-woven sponges, conforming bandages and non-adherent bandages).

Chronic venous insufficiency (CVI) results when the veins in the legs lose the ability to pump venous blood effectively. A range of problems result from leakage of fluid into the interstitial space and the area is then prone to ulceration.

VLUs constitute the majority of all leg ulcers accounting for 70-90% of wounds in lower extremities (see Snyder, *Clin. Dermatol.*, 23, 388 (2005)). Epidemiological data suggests that 1.5-3.0 people per 1,000 (0.15-0.3%) have active leg ulcers, rising to around 20 people per 1,000 (2%) in individuals over 80 years of age (see Valencia et al, *J. Am. Acad. Dermatol.*, 44, 401 (2001)). Consequently, VLUs are a massive economic burden. In Europe alone, the total annual cost is estimated at € 6.5 billion based on an average cost of € 7000 per episode (see Posnett, et al, *J. Wound Care*, 18, 154 (2009)). Expense is not limited solely to the direct cost of ulcer care, but includes indirect costs associated with disability and lost days at work.

Diabetic foot ulcers (DFUs) are one of the major complications in patients suffering from diabetes mellitus. Diabetes causes peripheral neuropathy with impaired sensory function and an increased risk of wounding. Circulatory impairment impedes the process of natural skin healing thereby resulting in HTH wounds. The risk of a patient with diabetes mellitus developing a foot ulcer is approximately 25% according to the International Diabetes Federation (see e.g. Boulton et al, *Lancet*, 366, 1719 (2005) and Singh et al, *JAMA*, 293, 217 (2005)). The annual incidence and prevalence of diabetic foot ulcers in patients with diabetes are 2-6% and 4-10%, respectively (see also Ramsey et al, *Diabetes Care*, 22, 382 (1999)). In addition, 10% of diabetic patients have contributing factors such as peripheral neuropathy and vascular complications for developing foot ulcers. DFUs are prone to infections leading to significant morbidity, and are associated with 25-90% of all amputations in this patient population (see also Ragnarson-Tennvall et al, *Diabetologia*, 44, 2077 (2001)).

DFUs also represent a significant economic burden. In Europe, DFUs that do not heal within 12 months cost an average of € 20,000 per patient (Prompers et al, *Diabetologia*, 51, 1826 (2008)).

There is no evidence to support that standard dressing materials are of any significant benefit to treat the aforementioned HTH ulcers, even when used in conjunction with other standard measures (cleansing, debridement, bandaging, etc.). In Europe, Regranex® (becaplermin) gel is indicated for the treatment of lower extremity diabetic neuropathic ulcers that extend into the subcutaneous tissue or beyond and have an adequate blood supply. It is used as an adjunct to, and not a substitute for, good ulcer care practices including initial sharp debridement, pressure relief and infection control. Although Regranex is the only drug product approved for treatment of such HTH ulcers, it has no documented effect on VLUs.

Thus, there is an urgent need for improved treatments of chronic wounds, and in particular HTH ulcers such as VLUs and DFUs.

LL-37 is derived from the 18-kDa human cathelicidin antimicrobial protein 18 (hCAP18). It is an important mediator in tissue repair and defense against infection. Both hCAP18 and LL-37 are present in various body fluids, including wound fluid (see, for example, Murakami et al, *J. Dent. Res.*, 81, 845 (2002), Schaller-Bals et al, *Am. J. Respir. Crit. Care Med.*, 165, 992 (2002) and Sorensen et al, *J. Biol. Chem.*, 278, 28540 (2003)). Although, in acute wounds, transcription of hCAP18/LL-37 is up-regulated within a few hours, and LL-37 is expressed at the wound margin by basal epidermal keratinocytes, chronic wounds have no LL-37 immunoreactivity at the wound edge (see, for example, Dressel et al, *Exp. Dermatol.*, 19, 628 (2010) and Rivas-Santiago et al, *J. Derm. Sci.*, 65, 19(2012)).

In vivo studies with synthetic LL-37 have shown that subcutaneous injection stimulates angiogenesis (Koczulla et al, *J. Clin. Invest.*, 111, 1665 (2003)), and repeated topical administration in acute wounds attracts inflammatory cells to the surrounding tissue. Antibodies against LL-37 inhibited healing in an ex vivo model of human acute wounds (Heilborn et al, *J. Invest. Dermatol.*, 120, 379 (2003); see also international patent application WO 2004/067025), while topical treatment with LL-37 stimulated wound healing in mice treated with a corticosteroid to impair normal healing (Ramos et al, *Peptides*, 32, 1469 (2011)). Administration of LL-37 in acute wounds of diabetic mice with impaired wound healing has shown beneficial effect in one study (Carretero et al, *J. Invest. Dermatol.*, 128, 223 (2008)), while other studies have failed to show an effect (Steinstraesser et al, *PLoS ONE*, 7, e39373 (2012)). EP 1 358 888 discloses that LL-37 is an inducer of angiogenesis.

International patent application WO 2009/001087 discloses wound care products in which LL-37 is impregnated into a solid substrate (a dressing) comprising a wound care material. There is no suggestion in that document that it is necessary to apply a certain dose of LL-37 in a formulation per unit wound area to treat the wound effectively. There is certainly no suggestion that there may be an upper limit to that dose, let alone what that limit might be.

DISCLOSURE OF THE INVENTION

Brief Description of the Drawings

FIG. 1 shows estimates from a "broken stick" analysis of wound healing rates by applying formulations comprising different concentrations of LL-37 to HTH VLUs, in which the solid line represents the placebo group, the large dashed line represents 3.2 mg/mL group, the smaller dashed line represents 1.6 mg/mL group, and the dotted line represents 0.5 mg/mL group.

The inventors have now found, in the clinical setting, that certain doses of LL-37 can be applied to treat effectively HTH/chronic leg ulcers. In particular, as described below, the inventors have found, surprisingly, that doses of at least about 80 µg of LL-37 applied per cm$^2$ of ulcer/wound area do not effectively treat chronic ulcers, including VLUs.

According to the invention therefore, there is provided a method for topically treating a chronic ulcer, such as a VLU or a DFU, which method comprises:
  (a) topical application to said ulcer of a pharmaceutical formulation comprising LL-37 or a pharmaceutically-acceptable salt thereof and one or more pharmaceutically-acceptable diluent or carrier system; followed by
  (b) application of a dressing,
wherein said application of said formulation provides for a dose of LL-37 at the wound site that is below about 80 µg of LL-37 applied per cm$^2$ of wound area to treat said ulcer.

There is further provided said pharmaceutical formulation for use at said dose in said method to treat a chronic ulcer, as well as the use of LL-37 for the manufacture of a pharmaceutical formulation for use at said dose in said method to treat a chronic ulcer.

The amino acid sequence of human LL-37 is shown below in SEQ ID NO:1:

[SEQ ID NO: 1]
LLGDFFRKSKEKIGKEFKRIVQRIKDFLRNLVPRTES

LL-37 may be employed in the form of a pharmaceutically acceptable base addition salt, including those of alkali metal cations (e.g. potassium and sodium) and alkaline earth metal cations (e.g. calcium and magnesium), ammonium or water-soluble amine addition salts such as N-methylglucamine-(meglumine), and the lower alkanolammonium and other base salts of pharmaceutically acceptable organic amines, among others. LL-37 may be used in the form of an acetate salt.

The method/uses of the invention are particularly useful in the treatment of chronic ulcers, including HTH ulcers, venous ulcers, diabetic ulcers and pressure ulcers, Ulcers that may be mentioned in particular include DFUs and, particularly, leg ulcers, such as VLUs.

As described hereinafter, in the specific formulations exemplified herein, a concentration of 0.5 mg of LL-37 per mL of the specific vehicle that was employed, when applied every third day to the ulcer, was calculated to provide an efficacious dose of about 13 µg of LL-37 per cm$^2$ of wound area. A concentration of 1.6 mg/mL gave an efficacious dose of 40 µg/cm$^2$. However, a concentration of 3.2 mg/mL, resulting in 80 µg/cm$^2$, gave rise to no clinical benefit.

Accordingly, the dose of LL-37 that is applied per cm$^2$ of the wound area to treat ulcers may be below a value within the range of about 40 µg and about 80 µg of LL-37 (in other words, below a value that is between about 40 µg and about 80 µg of LL-37). Suitable upper limits for the dose of LL-37 that is applied to the ulcer may be about 75 µg of LL-37 applied per cm$^2$ of wound area, such as about 70 µg/cm$^2$, for example about 65 µg/cm$^2$, or 60 µg/cm$^2$, including about 55 µg/cm$^2$, such about 50 µg/cm$^2$ or about 45 µg/cm$^2$. Suitable lower limits of LL-37 applied per cm$^2$ of wound area may be about 1 µg, such as about 3 µg, including about 5 µg, such as about 10 µg/cm$^2$, for example about 15 µg/cm$^2$, or 20 µg/cm$^2$, including about 25 µg/cm$^2$, such about 30 µg/cm$^2$ or about 35 µg/cm$^2$.

The inventors have found that chronic ulcers, such as VLUs and DFUs, may be effectively treated with doses below about 80 µg of LL-37 applied per cm$^2$ of wound area when applied every third day, which translates to about 26.7 µg of LL-37 applied per cm$^2$ of wound area for each day of treatment.

By "pharmaceutical formulation that provides for a dose of LL-37 that is below about 26.7 µg per cm$^2$ of wound area per day of treatment", we include or mean that the:
  (i) formulation is of a nature; and/or
  (ii) frequency of application of the formulation is such, that the amount of LL-37 that is available at the wound site to treat the ulcer does not exceed about 26.7 µg per cm$^2$ of wound area for each day of treatment.

To elucidate, in the specific formulations exemplified hereinafter, a concentration of 0.5 mg of LL-37 per mL of the specific vehicle that was employed (i.e. the specific pharmaceutical formulation described hereinafter), when applied every third day, provided an efficacious dose of about 13 µg of LL-37 per cm$^2$ of wound area, corresponds to about 4.3 µg of LL-37 per cm$^2$ of wound area for each day of treatment. Similarly, a concentration of 1.6 mg/mL gave an efficacious dose of 13.3 µg/cm$^2$ for each day. However, a concentration of 3.2 mg/mL resulted in 26.7 µg/cm$^2$ for each day, but gave rise to no clinical benefit.

In this respect, it is anticipated that concentrations that are lower than about 0.5 mg of LL-37 per mL of the same, specific vehicle employed, if applied more frequently (e.g. every day), may give rise to more LL-37 being available at the wound site to treat the ulcer, and so provide for a clinical benefit. The same applies to concentrations of about 3.2 mg/mL or more of the same, specific vehicle, applied less frequently than every three days.

Similarly, if a different formulation (for example a more extended and/or a slow release formulation) is employed, the amount of LL-37 that is available at any one time to treat the ulcer will be lower than is the case in the formulation specifically exemplified hereinafter. This will result in less LL-37 being available at the wound site to treat the ulcer at any given time. Accordingly, a higher concentration of LL-37 may be used initially in such a formulation to ensure that a similar amount of LL-37 is available at the wound site to treat the ulcer at any given time. Such a formulation may also be applied less frequently to give rise to the same effect.

According to a further aspect of the invention, there is provided a method of treatment of a chronic ulcer, which method comprises:
  (a) topical application to said ulcer of a pharmaceutical formulation comprising LL-37 and one or more pharmaceutically-acceptable diluent or carrier system; followed by
  (b) application of a dressing, wherein said application of said formulation provides for a dose of LL-37 at the wound site that is below about 26.7 µg (for example a dose that is below a value that is between about 13.3 µg and about 26.7 µg) of LL-37 applied per cm² of wound area for each day of treatment to treat said ulcer.

The pharmaceutical formulation that may be employed in the method of the invention can be formulated for direct (as defined herein) topical application to an ulcer. Non-limiting examples of such formulations are liquid or semi-solid formulations, and include any solution, suspension, emulsion, cream, gel or lotion, provided that it is sufficiently viscous enough at room temperature (e.g. between about 20° C. and about 25° C.) and at atmospheric pressure (e.g. about 1 atmosphere) that it is capable of physically remaining, in a coherent state, at the wound site following its application.

The liquid or semi-solid formulation should be viscous, and thus not be completely free-flowing, e.g. under the influence of gravity, at room temperature and at atmospheric pressure. However, it should also not so be so viscous at room temperature and at atmospheric pressure that it is an essentially solid state, and thus incapable of being manipulated with normal and/or reasonable manual pressure, using an appropriate medical instrument, to e.g. spread it over the wound. Formulations may also be applied to wounds by spraying using an appropriate spray (e.g. pump-action or aerosol) device to deliver the defined dose per unit wound area (see, for example, international patent application WO 2011/056116).

Thus, suitable viscosities for the formulation will depend upon the excipients that are employed, but may be in the range of about 1 to about 100 Pas, such as about 50 Pas, e.g. about 25 Pas, including about 15 or about 10 Pas. The aforementioned viscosity values are dynamic viscosities at room temperature (as hereinbefore defined) and atmospheric pressure (as hereinbefore defined), as measured by a standard viscometer or rheometer.

Pharmaceutical formulations that may be used to apply LL-37 to ulcers include aqueous solutions. An aqueous solution is a solution having physiologically- or pharmaceutically-acceptable properties (in relation to pH, ionic strength, isotonicity, etc). For example, isotonic solutions comprising water and other biocompatible solvents, aqueous solutions, such as saline and glucose solutions, and hydrogel-forming materials, may be employed. The aqueous solution can be buffered, with for example acetate buffer.

The pharmaceutical formulation may also comprise pharmaceutically-acceptable excipients, such as preservatives to prevent microbial growth, antioxidants, tonicity-modifying agents, colouring agents and the like. In aqueous suspensions, the compositions can be combined with suspending and stabilising agents.

In one aspect of the invention, LL-37 is dissolved in an aqueous solvent (e.g. water or acetate buffer) and an appropriate thickening agent added to create a viscous, spreadable aqueous soft gel, cream or lotion formulation.

When formulated in aqueous solutions, LL-37 may also be formulated along with a thickening agent in order to obtain a cream, gel or lotion of sufficient viscosity as described hereinbefore. Suitable agents, including hydrogel-forming materials, which includes synthetic polymers, such as polyvinylalcohol, polyvinylpyrrolidone, polyacrylic acid, polyethylene glycol, poloxamer block copolymers, and the like; semi-synthetic polymers, such as cellulose ethers, including carboxymethylcellulose, hydroxyethylcellulose, hydroxypropylcellulose, methylcellulose, hydroxypropylmethylcellulose and ethylhydroxyethylcellulose, and the like; natural gums, such as acacia, carrageenan, chitosan, pectin, starch, xanthan gum and the like. Such materials that may be mentioned include pharmaceutical grade polyvinylalcohols (for example with degrees of hydrolysis in the range of about 70 and about 99% (e.g. between about 85 and about 89%), and molecular weights in the range of about 15,000 and about 130,000).

It may be advantageous to use a formulation that is bio- and/or mucoadhesive.

It is key that the skilled reader understands however that, once he or she is in possession of the relevant information presented herein, regarding the maximum amount of LL-37 that should be applied per unit area of the wound (including per day of treatment), he or she will be able to ascertain, using routine techniques, for the excipients (i.e. the diluent(s), carrier(s), the thickening agent(s) and the other ingredients) that are employed, the correct concentration of LL-37 to use in that particular formulation to enable the appropriate dose per unit wound area (per day).

For example, the formulation can be tested in a bioassay for LL-37 activity and compared with LL-37 in phosphate-buffered saline (PBS). The bioassay may be an antimicrobial assay or an assay based on a response in a eukaryotic cell line. The concentration of LL-37 in the investigated formulation at which the biological effect is equivalent to the effect of a particular concentration of LL-37 in PBS (e g 10 µg/ml) can be used to calculate a dosing factor. For example, if a concentration of about 20 µg/ml of LL-37 in the investigated formulation is required to achieve the same biological effect as about 10 µg/ml of LL-37 in PBS, a dosing factor of about 2 can be derived which is used to double the concentration of LL-37 in the formulation and thus deliver the desired dose of LL-37 per wound area.

As will be appreciated by the skilled person, the above general routine technique is not applicable in the event that one or more of the excipients that is employed interacts with LL-37 to denude it, to substantially prevent its release from the formulation to the wound site, and/or to produce a synergistic effect, so resulting in the dose of LL-37 per unit wound area per day of treatment being outside the ranges mentioned hereinbefore. On the other hand, if an excipient enables a sustained release of LL-37 from the formulation, this should be taken into account when calculating the concentration to employ, as described above.

In the method/uses of the invention, a pharmaceutical formulation comprising LL-37 as described herein is first applied directly (i.e. without an intermediate step) and topically to the ulcer as described hereinbefore. Subsequently and separately to the application of the formulation, a dressing is separately applied. The subsequent and separate application of the dressing may, for example, take place no less than about 5 minutes, such as about 10 minutes (to allow binding of LL-37 to the wound tissue), but may also take place no more than about 20, such as about 30 minutes, of the application of the pharmaceutical formulation comprising LL-37.

Dressing materials that may be employed may be inert (i.e. substantially non-toxic) materials suitable for use in wound care and/or which are capable of aiding (for example, accelerating) the wound healing process and/or to preventing infection of a wound. For example, the dressing may be capable of enhancing epithelial regeneration and/or healing of wound epithelia and/or wound stroma. In one embodiment, the wound care product may be capable of enhancing the proliferation of epithelial and/or stromal cells.

The dressing may also be capable of absorbing wound exudate.

The dressing may thus comprise a material selected from the group consisting of alginates, sheet hydrogels, hydrofibres, foams and mixtures thereof.

Additional dressings, which are capable of absorbing wound exudate, include hydrocolloids, collagen-based materials, hyaluronic acid based materials, dextrinomers, dextrinomer/cadexomer and oxidised regenerated cellulose.

Dressings are typically provided in the form of a solid, dry non-woven sheet (or 'felt'), a freeze-dried sheet, a ribbon or a rope, and are particularly suitable for treating highly-exuding wounds.

Exemplary commercially available alginate-based materials include Suprasorb® (Sammons Preston, USA) and Kaltostat® (ConvaTec, UK).

The dressing may comprise or consist of a sheet hydrogel. Such wound care materials are particularly suitable for treating non-exuding wounds. Suitable sheet hydrogels may comprise one or more hydrogel-forming polymers selected from the group consisting of synthetic polymers, such as polyurethanes, polyvinylalcohol, polyvinylpyrrolidone, polyacrylic acid, polyethylene glycol, poloxamer block copolymers and the like; semi-synthetic polymers, such as cellulose ethers, including hydroxyethylcellulose, hydroxypropylcellulose, methylcellulose, methylhydroxypropylcellulose and ethylhydroxyethylcellulose, and the like; natural gums, such as acacia, carragenan, chitosan, pectin, starch, xanthan gum and the like; and alginates.

Exemplary sheet hydrogels available commercially include Elastogel® (Southwest Technologies Inc., USA) and Suprasorb® G (Sammons Preston, USA).

As a further alternative, the dressing may comprise or consist of a hydrofibre. Wound care products comprising such dressings are typically provided in the form of a dry, non-woven sheet, freeze-dried sheet, or a ribbon or rope, and are particularly suitable for use with light-to-heavy exuding wounds or wounds with both dry and wet regions.

Suitable hydrofibres may comprise or consist of carboxymethylcellulose, and include Aquacel® and Versiva® (both ConvaTec, UK) and Solvaline® N (Activa Healthcare, UK).

As a further alternative, the dressing may comprise or consist of a polyurethane foam, such as the Allevyn® range of products (Smith & Nephew, UK), Mepilex®, (Mölnlycke, Sweden) and Tegaderm® (3M, UK).

Prior to use, the pharmaceutical formulation and the dressing should be sterile and packaged in a microorganism-impermeable container. Sterility may be achieved using techniques well known in the art, such as aseptic manufacturing and/or final (i.e. post-production) sterilisation by irradiation.

As stated above, the dressing material should be inert, and thus not interact in any way with LL-37, for example to degrade it chemically or physically.

Dressings may thus also or alternatively comprise synthetic polymers, starches and/or polysaccharides. For example, the dressing may comprise an aqueous polymer matrix, a cellulose derivative, an acrylate copolymer, a gum, a polysaccharide and/or a polylactic acid polymer. Such materials may be water-soluble and/or may be perforated.

In the method/uses of the invention, the formulation comprising LL-37 is applied directly to the ulcer at the correct dosage as described above and the dressing thereafter applied to cover the treated wound area.

Optionally, a secondary conventional dressing may be applied over the top of the first dressing. Furthermore, in some cases, a permeable anti-adherence dressing may be applied somewhere between the ulcer and the dressing.

After application of the dressing, an appropriate compression means may advantageously be applied, including ductile, soft and absorbent cushions, such as Cellona® (Activa, UK) or Softban® (Smith & Nephew, UK), compression bandages, such as Comprilan® (Smith & Nephew), and/or medical stockings, such as ZipZoc® (Smith & Nephew).

The skilled person will appreciate that, prior to carrying out the method/uses of the invention, it may be necessary to remove dead, damaged or infected tissue (debridement), treat any infected tissue using an appropriate medical treatment (antiseptics), clean the wound area using an appropriate cleaning agent (e.g. water), and dry it using e.g. gauze. Curettage may also be conducted beforehand.

Moreover, and advantageously, the formulation and/or dressing may also be capable of preventing, abolishing, reducing or otherwise diminishing microbial growth in a wound environment. Thus, the formulation that is employed in the method/uses of the invention may further comprise an antimicrobial substance, for example a polypeptide selected from the group consisting of defensins, gramicidin S, magainin, cecropin, histatin, hyphancin, cinnamycin, burforin 1, parasin 1, protamines, and fragments, variants and fusion thereof which retain, at least in part, the antimicrobial activity of the parent protein; as well as silver, silver sulfadiazine, polyhexinide, iodine or metronidazole.

It will be appreciated that, in the method/uses of the invention, the formulation, dressings and/or compression means should be replaced on the wound at regular intervals, to aid the healing process and to prevent infection.

Whenever the word "about" is employed herein, particularly in the context of in relation to amounts, including doses of LL-37 and concentrations in formulations, timings, viscosities, dosing factors, degrees of hydrolysis, molecular weights, etc., it will be appreciated that such variables are approximate and as such may vary by ±10%, for example ±5% and preferably ±2% (e.g. ±1%) from the numbers specified herein.

The method/uses of the invention provide a wound care means that is easy and inexpensive to manufacture, and which enable the effective treatment of chronic wounds, including VLUs, DFUs and the like.

The method/uses of the invention also have the advantage that they employ using established pharmaceutical processing methods and employ materials that are approved for use in foods or pharmaceuticals, medical device products, or of like regulatory status.

The method/uses of the invention may also have the advantage that they may be more efficacious than, produce fewer side effects than, possess a better patient acceptability than, have a better pharmacokinetic profile than, and/or have other useful pharmacological, physical, or chemical properties over, similar methods known in the prior art, whether for the treatment of chronic wounds, such as VLUs, DFUs, or otherwise.

The invention is illustrated by way of the following example, with reference to the attached FIG. 1, which shows estimates from a "broken stick" analysis of wound healing rates by applying formulations comprising different concentrations of LL-37 to HTH VLUs, in which the solid line represents the placebo group, the large dashed line represents 3.2 mg/mL group, the smaller dashed line represents 1.6 mg/mL group, and the dotted line represents 0.5 mg/mL group.

EXAMPLE

Double-Blind, Randomised, Placebo-Controlled, Safety and Pilot-Dose Response Study of LL-37 in HTH VLUs A double-blind, randomised, placebo-controlled, Phase I/II safety and pilot-dose response study was conducted on human subjects. The first subject was enrolled in August 2012 and the last subject completed in April 2013.

The study was designed, conducted and reported in accordance with the International Conference on Harmonisation (ICH) Harmonised Tripartite Guidelines for Good Clinical Practice (GCP), with applicable local regulations and ethical principles laid down in the Declaration of Helsinki and was conducted across three centres in Sweden.

Selection Criteria

Study subjects comprised either male subjects of at least 18 years of age, or post-menopausal or clinically sterile women, with VLUs or combined venous-arterial ulcers with a predominant venous component.

Exclusion criteria included if subjects had known predominant aetiology other than VLU within the target ulcer, and malignant disease (excluding basal cell carcinoma), unless in remission for 5 years or more.

After obtaining necessary regulatory (Swedish Medicinal Products Agency (MPA) and ethical (regional Ethics Committee) approvals, and written informed consent, a total of 56 subjects attended a screening visit followed by a 3-week open-label run-in period.

Target wounds with an area greater than 30 $cm^2$ and less than 2 $cm^2$ were excluded initially. However, in order to increase the inclusion rate and decrease the total study time, criteria were amended after randomisation of 21 subjects, to exclude areas greater than 40 $cm^2$ and less than 1 $cm^2$. If an eligible subject had more than one wound satisfying the entry criteria, the investigator identified the wound with the most appropriate size, shape and localisation as target wound. Only one wound per subject was treated in the study.

During the 3-week run-in period, subjects received, every third day (±1) and not more than two times per week, six applications (in total) of a placebo preparation (see below) in combination with standard compression bandaging (as defined by the Swedish MPA), comprising elastic bandaging and appropriate dressing to control wound exudation.

If the ulcerative area decrease was greater than between 7% and 13% (depending on size) per week relative to the start of the run-in period, the ulcer was not defined as HTH for the purposes of this study. In such cases, subjects were excluded from the study and the outcome was recorded as screening failure.

After a run-in period, 34 eligible subjects underwent baseline assessments before randomisation to receive active treatment (one of three treatment strengths) or placebo.

Formulations and Treatment

Following the above run-in period, a 4-week treatment period was initiated, including 8 visits, an end-of-treatment visit 3 days (±1 day) after the last treatment, and a follow-up visit after an additional 4 weeks (±1 to 7 days).

Subjects were randomised into four treatment groups to receive LL-37 (one of three alternative strengths), or placebo.

Wound bed preparation prior to treatment included debridement of non-viable tissue, treatment of clinical infection and selection of the most appropriate dressing (see below). The wound was cleaned using tap water, gently dried with a gauze pad and, if necessary, curettage was applied prior to application of the trial product or placebo.

0.7 mL of a sterile concentrate of LL-37 in water at concentrations of 2.5, 8 or 16 mg of LL-37 per mL was provided in sealed glass vials (APL, Umeå, Sweden), which were stored prior to the trial at between 2 and 8° C. Immediately before application to the wound, this was diluted with 5 mL of a viscous diluent solution comprising 13.1% (w/w) of polyvinyl alcohol in acetate buffered saline (APL AB) to give final concentrations of either 0.5, 1.6 or 3.2 mg/mL, respectively. Placebo comprised exactly the same solution, but without LL-37 present.

The diluted viscous liquid solution of active treatment or placebo was applied topically at an amount of 25 μL/$cm^2$ with a 1 mL graded syringe at the centre of the cleansed and dried ulcer, and distributed evenly over the entire ulcer area using the rounded head of the syringe plunger that had been used in mixing the study drug.

After a 5-minute wait (to prevent LL-37 or placebo from being absorbed by the dressing material), the above procedure was followed by application of a dressing and a compression bandage.

For moderate to heavy exudating wounds, highly absorbent dressings made of polyurethane foam, such as Mepilex®, Allevyn® and Tegaderm®, were used. Alternatively, the absorbent hydrofibre dressing Aquacel® was used. For slight to moderate exudative wounds, non-adherent dressings were used, with or without an adhesive edge. The dressings used were Solvaline® N or the combined polyurethane/hydrofibre dressing Versiva®. For dry wounds, Aquacel® hydrofibre dressing was used.

In combination with these other dressings, gauze pads were used to offload sensitive parts during compression. A 100% viscose, ductile, soft and absorbent cushion was used, including Cellona® or Soffban®. Comprilan® was the most commonly used compression bandage used in the study. Two bandages (8 and 10 cm wide) were tied with approximately 50% stretch from the base of the toes in a spiral to just beneath the knee. Alternatively, ZipZoc® medical stocking plus Coplus® or a similar self-adhesive bandage or Profore Lite® in combination with some of the above mentioned wound dressings were allowed. A long-stretch bandage of Dauer-type could also be used. Because of the high resting pressure with this type of bandage, it was temporarily removed during the night or when the subject was in a resting position for a long period.

Additional treatment included specific topical creams for the treatment of skin problems. Zinc paste or Cavilon® were used on per-ulcer skin to protect the skin near the wound edge from maceration. Hydrocortisone cream or ointment (topical steroid group I or hydrocortisone-imidazole cream) was used for peri-ulcer eczema. If the skin was dry and scaly, Canoderm or Propyderm cream was allowed.

The above procedure was repeated every third day (±1) over a 4 week treatment period, not more than two times per week, representing a total of eight applications.

Subsequent to treatment, subjects were followed up for a period of 4 weeks (±1 to 7 days).

The study assessed the rate of wound healing, pain at wound site both at the time of dressing and over the previous 24 hours using Visual Analogue Scale (VAS). Any incidence of complete healing was recorded even though statistically significant results were not expected based on the short duration of the trial and the small sample size. Wound size measurements were performed repeatedly over the study period to indicate the extent of wound healing. At every other visit, wound area was measured using the Visitrak™ planimetry device, pain at the wound site and wound characteristics (odour, slough, granulation and necrotic tissue) were recorded. The wound condition was to be described using photographs of the wound.

Adverse events (AEs) and local tolerability were assessed at all visits. Subjects were advised to report any AEs and were given an emergency card with a phone number to call in case of any significant AEs. Blood was collected for laboratory safety assessment and investigation of development of antibodies against LL-37. Changes in laboratory values and vital signs were assessed, and analysis of autoantibody formation against LL-37 was performed.

Safety endpoints included:
incidence of severe local reactions in wound and adjacent skin as exemplified by clinical signs of inflammation (oedema, redness, odour and raised temperature) or skin irritation (scaling, redness, papules, vesicles, pustules); any local reaction was recorded on a graded scale (0 to 3);
incidence of greater than 30% increase in wound area relative to baseline (randomisation visit);
change in laboratory values and vital signs from baseline;
overall incidence of AEs.

Efficacy endpoints included:
wound healing rate within the study period;
a number of ulcers attaining a greater than 30% area reduction from baseline at randomization; and
changes in local pain using VAS score (0 to 10)
changes in wound characteristics: (scores for slough, exudation, granulation tissue, necrosis) from baseline (scale 0 to 3).

Analyses

Statistical analyses were carried out using SAS® software (version 9.2 or higher; SAS Institute, Cary, N.C., US).

The wound area was modelled over time for each subject to estimate the healing rate over the treatment period and the relationship between healing rate and dose was investigated.

Estimates of healing rate constants (i.e. the change in wound area or mathematically transformed wound area/day) were derived with 95% confidence intervals (CIs) for each of the four treatment groups. An exponential decay model was fitted to the data with two parameters representing the initial wound area and the rate of healing. The model was of the form:

$$Y = \alpha \times e^{\beta t}$$

where α denotes the initial wound area (i.e. at randomisation visit), β denotes the reduction in size expressed as healing rate per day, Y denotes the wound area and t denotes the time in days from the randomisation visit.

Additional analyses incorporating all run-in data was conducted to assess how the application of study treatments affected the healing process. This was assessed using a "broken-stick" approach, approximating pre- and post-randomisation data by a linear response over time after suitable data transformation (e.g. log, square root).

If appropriate, pain scores were analysed using a repeated measures analysis to assess the overall difference between treatments over time. The model included terms for treatment, and time and the interaction between the two.

The incidence of any AEs was estimated using the percentage of subjects in each treatment group who experienced at least one AE, with associated 95% CIs. CI was calculated using the method detailed in Altman et al, *Statistics with Confidence*, BMJ Publication Group (2000), which was appropriate for small samples, or low incidences. The relationship between incidence of AEs and dose was investigated if appropriate. The overall incidence of grade 3 (severe) local reactions was presented for the LL-37 treated subjects with 95% CIs. Laboratory data were to be shown in plots of post-treatment values versus baseline, with reference ranges.

Results

A total of 31 subjects received the full course of eight treatment applications. Of the remaining three subjects, two (in 0.5 mg/mL treatment group) received seven applications and one subject (in placebo arm) received three applications.

The exponential decay model fitted to the wound area provided a good fit to the data.

The healing rate constant for the 0.5 mg/mL dose of LL-37 (0.039) differed significantly from that for placebo (0.007, p=0.003) representing a faster reduction in wound area (i.e. improved healing). A non-linear mixed effect model was used and the significance of the difference between the parameters was calculated by taking the estimate of the difference and dividing by its standard error, and comparing the result against a t-distribution.

The estimated healing rate constant for the 1.6 mg/mL dose of LL-37, 0.019, also represented a faster reduction in wound area compared to placebo, although was not statistically significant at the 5% level (p=0.09). There was no statistically significant difference between the highest dose of LL-37 (healing rate constant 0.004) group and the placebo group. The low and intermediate dose groups were statistically indistinguishable. The estimated healing rate constants, with a measure of mean reduction in wound area, for each treatment are shown in Table 1 below.

TABLE 1

Estimates of wound healing rates

| Treatment | Estimated initial area (cm²) Mean (95% C.I.) | Estimated healing rate constant[1] (cm²/day) Mean (95% C.I.) | Estimated difference relative to control (cm²/day) Mean (95% C.I.) | p-value |
|---|---|---|---|---|
| Placebo (n = 9) | 9.222 (6.133 to 12.312) | 0.007 (−0.001 to 0.014) | | |
| LL-37 0.5 mg/mL (n = 8) | 5.036 (1.742 to 8.329) | 0.039 (0.020 to 0.058) | 0.032 (0.012 to 0.053) | 0.003 |
| LL-37 1.6 mg/mL (n = 9) | 7.498 (4.583 to 10.414) | 0.019 (0.007 to 0.031) | 0.012 (−0.002 to 0.026) | 0.088 |
| LL-37 3.2 mg/mL n = 8 | 5.872 (2.573 to 9.171) | 0.004 (−0.007 to 0.015) | −0.003 (−0.016 to 0.010) | 0.656 |

[1]Where the lower 95% confidence limit is negative this represents a positive healing rate constant over time since the model fitted assumes a negative constant (i.e. decrease in wound area).

Overall, the highest reduction in wound area was noted for 1.6 mg/mL dose of LL-37 across all visits. The mean reduction in wound area for 1.6 mg/mL dose of LL-37 was 5.29 cm² from randomization to the end of the study (see Table 2 below).

TABLE 2

Wound Area (cm²) at Each Visit

| | Mean ± S.D for the visits | | | |
|---|---|---|---|---|
| | Placebo (N = 9) | LL-37 0.5 mg/mL (N = 8) | LL-37 1.6 mg/mL (N = 9) | LL-37 3.2 mg/mL (N = 8) |
| Visit 1 (Screening) | 9.72 ± 8.475 | 4.59 ± 2.024 | 7.84 ± 4.789 | 8.41 ± 6.450 |

TABLE 2-continued

Wound Area (cm²) at Each Visit

| | Mean ± S.D for the visits | | | |
|---|---|---|---|---|
| | Placebo (N = 9) | LL-37 0.5 mg/mL (N = 8) | LL-37 1.6 mg/mL (N = 9) | LL-37 3.2 mg/mL (N = 8) |
| Visit 3 | 10.25 ± 9.875 | 4.39 ± 1.995 | 8.14 ± 4.997 | 7.83 ± 6.163 |
| Visit 6 (Randomisation) | 9.54 ± 8.246 | 5.11 ± 1.732 | 7.69 ± 4.072 | 8.50 ± 6.919 |
| Visit 8 | 8.60 ± 8.171 | 3.89 ± 1.329 | 5.83 ± 2.156 | 7.95 ± 6.270 |
| Visit 10 | 6.63 ± 5.569 | 3.18 ± 1.549 | 5.34 ± 1.943 | 7.03 ± 5.063 |
| Visit 12 | 6.50 ± 7.777 | 2.26 ± 1.061 | 4.59 ± 2.266 | 5.93 ± 5.317 |
| Visit 14 | 6.16 ± 6.850 | 1.93 ± 1.262 | 3.86 ± 3.029 | 5.89 ± 4.784 |
| Visit 15 (End of Treatment) | 6.52 ± 7.683 | 1.98 ± 1.276 | 3.34 ± 3.166 | 5.85 ± 4.648 |

SEQUENCE LISTING

```
<160> NUMBER OF SEQ ID NOS: 1

<210> SEQ ID NO 1
<211> LENGTH: 37
<212> TYPE: PRT
<213> ORGANISM: Artificial Sequence
<220> FEATURE:
<223> OTHER INFORMATION: Synthetic Peptide

<400> SEQUENCE: 1

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser
            35
```

TABLE 2-continued

Wound Area (cm²) at Each Visit

| | Mean ± S.D for the visits | | | |
|---|---|---|---|---|
| | Placebo (N = 9) | LL-37 0.5 mg/mL (N = 8) | LL-37 1.6 mg/mL (N = 9) | LL-37 3.2 mg/mL (N = 8) |
| Visit 16 (End of Study) | 5.76 ± 7.574 | 1.33 ± 1.209 | 2.40 ± 3.269 | 6.19 ± 4.770 |

SD: Standard deviation; end of study refers to the follow-up visit performed approximately 4 weeks after the last treatment.

The healing rate constant for the exponential decay model exhibited a 6-fold difference for the lowest dose (0.5 mg/mL) group, and a 3-fold difference for the intermediate dose (1.6 mg/mL) group versus the placebo group (p=0.003 for 0.5 mg/mL and p=0.088 for 1.6 mg/mL). These formulations thus gave rise to a faster reduction in wound area, and thus an improved healing response. However, there was no difference between the estimated healing rates in the highest LL-37 dose (3.2 mg/mL) group and the placebo group.

In order to incorporate the data from the run-in and to assess if the addition of treatment affected the rate of healing, a broken stick analysis was conducted and was consistent with the previous analyses. As shown in FIG. 1, both the lower two doses of LL-37 had greater reduction in wound area after randomisation than during the run-in, indicating statistically significant improved healing compared to pre-treatment values (p<0.001 and p=0.011 for 0.5 mg/mL and 1.6 mg/mL respectively). No significant difference between the post-randomisation rate and the run-in was seen for either the highest dose or placebo. The rate of change during the run-in was very close to zero, as would be expected since responders were excluded from the study.

CONCLUSIONS

A marked and significant improvement in wound healing was observed in response to administration of the two lower doses of LL-37 (0.5 and 1.6 mg/mL). The results from this study suggest that doses of 0.5 (which equates to 13 µg of LL-37 per cm² of wound area), and 1.6 mg/mL (which equates to 40 µg of LL-37 per cm² of wound area) every third day results in significant stimulation of wound healing. Alternatively, a less frequent application of a higher dose may be appropriate.

The invention claimed is:

1. A method of treating a chronic ulcer, wherein said method comprises:
   (a) topically applying to said chronic ulcer a pharmaceutical formulation, wherein the pharmaceutical formulation is an aqueous solution comprising LL-37 or a pharmaceutically-acceptable salt thereof, wherein the pharmaceutical formulation comprises one thickening agent being polyvinyl alcohol; followed by
   (b) topically applying a dressing to said chronic ulcer;
   wherein the dose of LL-37 applied per cm² of wound area is between about 1 µg/cm² and about 70 µg/cm², and wherein the pharmaceutical formulation has a viscosity in the range of about 2 and about 10 Pa·s.

2. The method as claimed in claim 1, wherein the dose of LL-37 applied per cm² of wound area is between about 5 µg/cm² and about 60 µg/cm².

3. A method of treating a chronic ulcer, wherein said method comprises:
   (a) topically applying to said chronic ulcer a pharmaceutical formulation, wherein the pharmaceutical formulation is an aqueous solution comprising LL-37 or a pharmaceutically-acceptable salt thereof, wherein the pharmaceutical formulation comprises one thickening agent being polyvinyl alcohol; followed by (b) topically applying a dressing to said chronic ulcer; wherein the dose of LL-37 applied per cm² of wound area is between about 0.3 µg/cm² and about 23.3 µg/cm² per day of treatment, and wherein the pharmaceutical formulation has a viscosity in the range of about 2 and about 10 Pa·s.

4. The method as claimed in claim 3, wherein the dose is between about 1.6 µg/cm² and about 20 µg/cm² per day of treatment.

5. The method as claimed in claim 1, wherein the chronic ulcer is a venous leg ulcer.

6. The method as claimed in claim 1, wherein the chronic ulcer is a diabetic foot ulcer.

7. The method as claimed in claim 2, wherein the chronic ulcer is a venous leg ulcer.

8. The method as claimed in claim 2, wherein the chronic ulcer is a diabetic foot ulcer.

9. The method as claimed in claim 3, wherein the chronic ulcer is a venous leg ulcer.

10. The method as claimed in claim 3, wherein the chronic ulcer is a diabetic foot ulcer.

11. The method as claimed in claim 4, wherein the chronic ulcer is a venous leg ulcer.

12. The method as claimed in claim 4, wherein the chronic ulcer is a diabetic foot ulcer.

13. A method of treating a chronic ulcer, wherein said method comprises:
(a) topically applying to said chronic ulcer a pharmaceutical formulation, wherein the pharmaceutical formulation is an aqueous solution consisting of i) LL-37 or a pharmaceutically-acceptable salt thereof; ii) polyvinyl alcohol; iii) a buffer; iv) water; and v) optionally one or more pharmaceutically acceptable excipients;
wherein the dose of LL-37 applied per cm² of wound area is between about 1 µg/cm² and about 70 µg/cm²; wherein the pharmaceutical formulation is a viscous liquid having a viscosity in the range of about 2 and about 10 Pa's; and
wherein the pharmaceutically acceptable excipient is selected from a preservative, an antioxidant, a tonicity modifying agent and a coloring agent.

14. A method of treating a chronic ulcer, wherein said method comprises:
(a) topically applying to said chronic ulcer an aqueous pharmaceutical formulation, wherein the pharmaceutical formulation is an aqueous solution consisting of i) LL-37 or a pharmaceutically-acceptable salt thereof; ii) polyvinyl alcohol; iii) a buffer; iv) water; and v) optionally one or more pharmaceutically acceptable excipients; followed by
(b) topically applying a dressing to said chronic ulcer;
wherein the dose of LL-37 is between about 0.3 µg/cm² and about 23.3 µg/cm² per day of treatment; wherein the pharmaceutical formulation is a viscous liquid having a viscosity in the range of about 2 and about 10 Pa·s; and
wherein the pharmaceutically acceptable excipient is selected from a preservative, an antioxidant, a tonicity modifying agent and a coloring agent.

* * * * *

UNITED STATES PATENT AND TRADEMARK OFFICE
CERTIFICATE OF CORRECTION

PATENT NO. : 10,226,508 B2
APPLICATION NO. : 15/037199
DATED : March 12, 2019
INVENTOR(S) : Alvar Grönberg et al.

Page 1 of 1

It is certified that error appears in the above-identified patent and that said Letters Patent is hereby corrected as shown below:

In the Claims

At Column 16, Claim number 13, end of Line number 3, after "excipients;" insert the following as Line 4: --(b) topically applying a dressing to said chronic ulcer;--

Signed and Sealed this
Ninth Day of July, 2019

Andrei Iancu
*Director of the United States Patent and Trademark Office*